United States Patent
Krekeler et al.

(10) Patent No.: US 11,072,605 B2
(45) Date of Patent: Jul. 27, 2021

(54) CRYSTALLINE BREXPIPRAZOLE

(71) Applicant: Hexal Aktiengesellschaft, Holzkirchen (DE)

(72) Inventors: Andreas Krekeler, Holzkirchen (DE); Michael Sedlmayr, Holzkirchen (DE)

(73) Assignee: Hexal AG, Holzkirchen (DE)

( * ) Notice: Subject to any disclaimer, the term of this patent is extended or adjusted under 35 U.S.C. 154(b) by 0 days.

(21) Appl. No.: 16/481,206

(22) PCT Filed: Feb. 1, 2018

(86) PCT No.: PCT/EP2018/052589
§ 371 (c)(1),
(2) Date: Jul. 26, 2019

(87) PCT Pub. No.: WO2018/141886
PCT Pub. Date: Aug. 9, 2018

(65) Prior Publication Data
US 2019/0389847 A1 Dec. 26, 2019

(30) Foreign Application Priority Data

Feb. 2, 2017 (EP) .................................. 17154414
Nov. 29, 2017 (EP) .................................. 17204369

(51) Int. Cl.
*C07D 409/12* (2006.01)

(52) U.S. Cl.
CPC ........ *C07D 409/12* (2013.01); *C07B 2200/13* (2013.01)

(58) Field of Classification Search
CPC .... C07D 409/12; A61K 31/4709; A61P 25/18
See application file for complete search history.

(56) References Cited

FOREIGN PATENT DOCUMENTS

| | | | |
|---|---|---|---|
| CA | 2871398 A1 | 10/2013 | |
| CN | 105106142 A | 12/2015 | |
| EP | 2868318 A1 | 5/2015 | |
| WO | 2006112464 A1 | 10/2006 | |
| WO | 2012026562 A1 | 3/2012 | |
| WO | 2013161830 A1 | 10/2013 | |
| WO | 2013162046 A1 | 10/2013 | |

OTHER PUBLICATIONS

N.E. Sharpless et al., Nature Reviews Drug Discovery 1-14, 2 (2006).*
J.H. Poupaert, Drug Design: Basic Principles and Applications, in 2 Encyclopedia of Pharmaceutical Technology 1362-1369, 1367 (James Swarbrick ed., 3rd ed., 2007).*
L.I. Zon et al., Nature Reviews Drug Discovery 4, 35 (2005).*
European Medicines Agency, Guideline on the sterilisation of the medicinal product, active substance, excipient and primary container, 2019, 25 pages.
International Search Report and Written Opinion for PCT/EP2018/052589, dated Aug. 9, 2018, 11 pages.

* cited by examiner

*Primary Examiner* — Deepak R Rao
(74) *Attorney, Agent, or Firm* — Luedeka Neely Group, P.C.

(57) ABSTRACT

The present invention relates to crystalline brexpiprazole having a particle size distribution (PSD) characterized by a d(90) of 30 μm to 100 μm, by a d(10) of at least 1.0 μm, and by a d(4,3) of at least 15.0 μm. The present invention also relates to a pharmaceutical composition comprising a crystalline brexpiprazole having a PSD characterized by a d(90) of 30 μm to 100 μm, by a d(10) of at least 1.0 μm, and by a d(4,3) of at least 15.0 μm, and to an aqueous suspension comprising said crystalline brexpiprazole. The present invention also relates to a composition comprising a crystalline brexpiprazole having a PSD characterized by a d(90) of 30 μm to 100 μm, by a d(10) of at least 1.0 μm, and by a d(4,3) of at least 15.0 μm, wherein said composition is essentially free from secondary particles of brexpiprazole. The present invention also relates to an injectable preparation, vial, prefilled syringe, or kit, comprising crystalline brexpiprazole having a PSD characterized by a d(90) of 30 μm to 100 μm, by a d(10) of at least 1.0 μm, and by a d(4,3) of at least 15.0 μm. The present invention also relates to a process for the preparation of an aqueous suspension, a vial, a prefilled syringe, or a lyophilisate, comprising a step of incorporating crystalline brexpiprazole having a PSD characterized by a d(90) of 30 μm to 100 μm, by a d(10) of at least 1.0 μm, and by a d(4,3) of at least 15.0 μm. Finally, the present invention also relates to crystalline brexpiprazole having a PSD characterized by a d(90) of 30 μm to 100 μm, by a d(10) of at least 1.0 μm, and by a d(4,3) of at least 15.0 μm, for use in the treatment or prevention of relapse of schizophrenia, bipolar disorder, or depression.

12 Claims, 1 Drawing Sheet

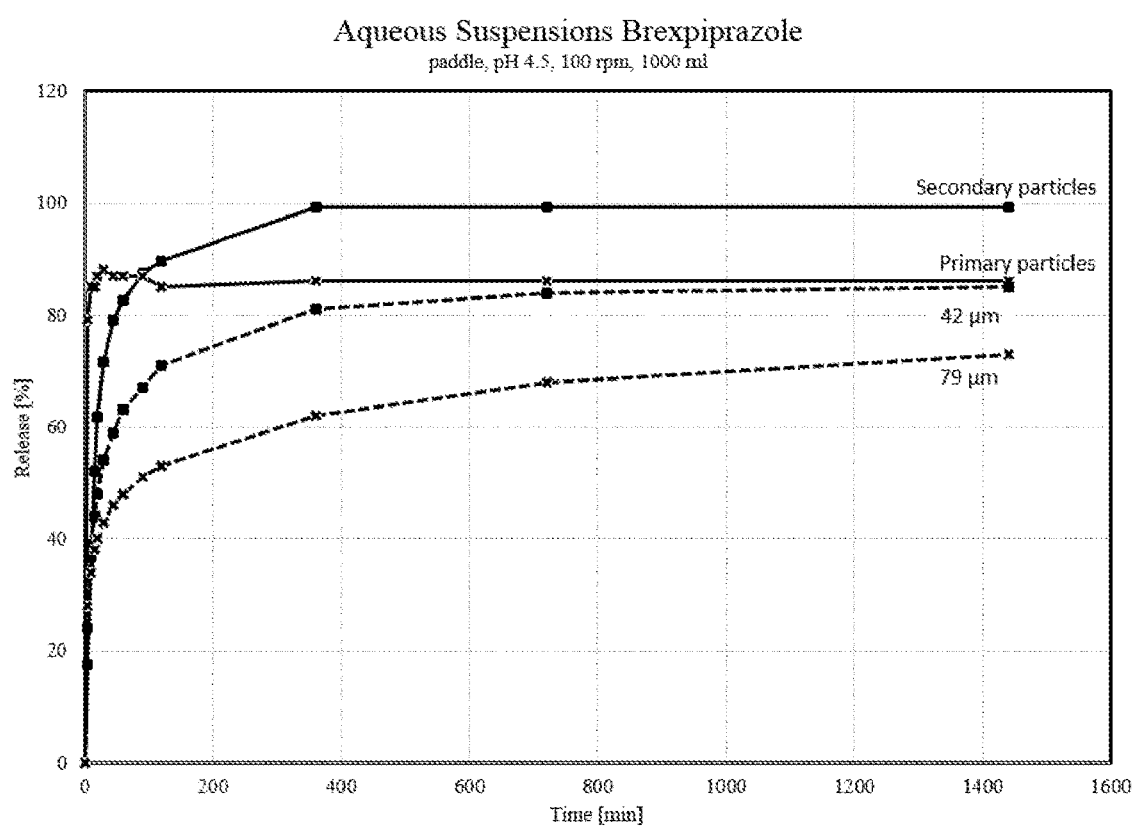

CRYSTALLINE BREXPIPRAZOLE

This application is a Section 371 national phase entry of PCT application PCT/EP2018/052589, filed Feb. 1, 2018. This application also claims the benefit of the earlier filing dates of European patent application 17154414.1, filed Feb. 2, 2017, and European patent application 17204369.7, filed Nov. 29, 2017.

FIELD OF THE INVENTION

The present invention relates to crystalline brexpiprazole having a particle size distribution (PSD) characterized by a d(90) of 30 μm to 100 μm, by a d(10) of at least 1.0 μm, and by a d(4,3) of at least 15.0 μm.

The present invention also relates to a pharmaceutical composition comprising a crystalline brexpiprazole having a PSD characterized by a d(90) of 30 μm to 100 μm, by a d(10) of at least 1.0 μm, and by a d(4,3) of at least 15.0 μm, and to an aqueous suspension comprising said crystalline brexpiprazole.

The present invention also relates to a composition comprising a crystalline brexpiprazole having a PSD characterized by a d(90) of 30 μm to 100 μm, by a d(10) of at least 1.0 μm, and by a d(4,3) of at least 15.0 μm, wherein said composition is essentially free from secondary particles of brexpiprazole.

The present invention also relates to an injectable preparation, vial, prefilled syringe, or kit, comprising crystalline brexpiprazole having a PSD characterized by a d(90) of 30 μm to 100 μm, by a d(10) of at least 1.0 μm, and by a d(4,3) of at least 15.0 μm.

The present invention also relates to a process for the preparation of an aqueous suspension, a vial, a prefilled syringe, or a lyophilisate, comprising a step of incorporating crystalline brexpiprazole having a PSD characterized by a d(90) of 30 μm to 100 μm, by a d(10) of at least 1.0 μm, and by a d(4,3) of at least 15.0 μm.

Finally, the present invention also relates to crystalline brexpiprazole having a PSD characterized by a d(90) of 30 μm to 100 μm, by a d(10) of at least 1.0 μm, and by a d(4,3) of at least 15.0 μm, for use in the treatment or prevention of relapse of schizophrenia, bipolar disorder, or depression.

BACKGROUND OF THE INVENTION

7-[4-[4-(1-Benzothiophen-4-yl)piperazin-1-yl]butoxy]quinolin-2(1H)-one (brexpiprazole; compound I) is an antidepressant and antipsychotic drug marketed under the brand Rexulti® for the oral treatment of schizophrenia and as an adjunctive treatment to antidepressants in major depressive disorder. Rexulti® tablets are intended for oral administration and available in 0.25 mg, 0.5 mg, 1 mg, 2 mg, 3 mg and 4 mg strengths. The product was approved in the U.S. in the year 2015 for the aforementioned indications and is currently in phase III trials for the treatment of agitation associated with Alzheimer's disease and the treatment of PTSD (post-traumatic stress disorder).

(I)

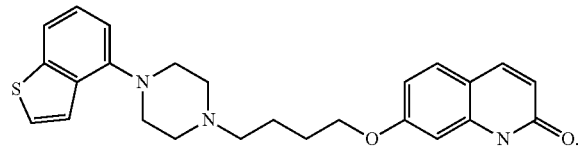

Brexpiprazole is an atypical antipsychotic and shows partial agonist activity at serotonin 5-HT1A and dopamine D2 receptors, and antagonist activity at serotonin 5-HT2A receptors.

WO 2006/112464 A1 discloses brexpiprazole and its use for the treatment of schizophrenia and other central nervous system disorders. Brexpiprazole is described in example 1 as a crystalline material obtained as a white powder by recrystallization from ethanol.

WO 2013/161830 A1 discloses an aqueous suspension comprising secondary particles formed by aggregation of brexpiprazole having a mean secondary particle diameter of 1 to 50 μm.

The aqueous suspension disclosed in WO 2013/161830 A1 is intended to be used as a sustained-release injectable that provides the effect of brexpiprazole for a prolonged period of time.

In WO 2013/161830 A1 sustained release of brexpiprazole while at the same time avoiding a "burst effect" of the injectable, i.e. a fast release of a fraction of the injected brexpiprazole, is suggested to be achieved by formulating an injectable composition comprising secondary particles of brexpiprazole. However, preparing secondary particles of an active pharmaceutical ingredient (API) such as brexpiprazole is comparably laborious, as certain measures have to be taken in order to arrive at said secondary particles. Moreover, the addition of additional compounds is necessary in order to arrive at secondary particles, making the injectable preparation of WO 2013/161830 A1 more complex in terms of preparing said injectable preparation, and also in terms of the various additional compounds that are present in said injectable preparation. Because of the latter, the preparation is more likely to cause an allergic reaction by the patient. Especially the particle binders of WO 2013/161830 A1 comprise compounds with surface-active properties which may cause adverse effects in vivo.

It is therefore an unmet need to provide brexpiprazole for an in injectable preparations so that such injectable preparations exhibit satisfying properties and/or improved performance, for example with regard to processability and/or dissolution profile, wherein said formulations are easy to prepare and/or are less likely to cause allergic reactions.

SUMMARY OF THE INVENTION

The present inventors have found that processability, and/or further properties, e.g. dissolution profile and/or complexity of composition, can be improved when crystalline brexpiprazole exhibiting a certain particle size distribution is provided, for example by critically observing specified parameters of a particle size distribution and correspondingly specifically selecting crystalline brexpiprazole complying with the specified parameters.

It was surprisingly found that when crystalline brexpiprazole exhibiting the particle size distribution (PSD) as defined herein is selected for a brexpiprazole-containing composition, such compositions (for instance pharmaceutical compositions such as injectables) that comprise the preparation of primary particles of brexpiprazole having the controlled PSD exhibit a dissolution profile that is at least comparably to, or even improved when compared to, the dissolution profile of comparative prior art compositions (such as comparative injectables) comprising secondary particles of crystalline brexpiprazole. For instance, it was beneficially found in the present invention that a burst effect, i.e. an initial release of brexpiprazole leading to undesired blood levels, can be avoided. Moreover, pharmaceutical compositions, such as injectable preparations, comprising the crystalline brexpiprazole exhibiting the PSD as defined herein are advantageous with regard to processability.

Moreover, since crystalline brexpiprazole exhibiting the PSD according to the present invention exhibits an acceptable or even improved dissolution profile, it is not necessary anymore to provide secondary particles of brexpiprazole, as it is the case in prior art. This enables improved processability and applying simpler formulation techniques: no time-consuming, costly measures, such as the addition of specific excipients that promote aggregation of brexpiprazole primary particles, have to be taken that would otherwise be necessary to obtain the conventionally sought secondary particles. This for instance additionally creates the possibility of formulating said crystalline brexpiprazole in dosage forms, such as injectables, without adding aggregation-promoters such as binders. In other words, by the provision and the use of the crystalline brexpiprazole exhibiting the particle size distribution (PSD) as defined herein, addition of certain excipients can be avoided, thereby minimizing the exposure of patients to potential allergens. At the same time a burst effect of an injectable comprising the crystalline brexpiprazole exhibiting the particle size distribution (PSD) as defined herein can be avoided.

Accordingly, the present invention provides the following aspects, subject-matter and preferred embodiments which, respectively taken alone or in combination, contribute to providing improved technical effects and to solving the afore-mentioned object of the invention:

1. Crystalline brexpiprazole, wherein the crystalline brexpiprazole has a particle size distribution (PSD) characterized by a d(90) of 30 μm to 100 μm, by a d(10) of at least 1.0 μm, and by a d(4,3) of at least 15.0 μm.

2. The crystalline brexpiprazole according to item 1, wherein the brexpiprazole is in the form of an anhydrate, or in the form of a hydrate comprising up to two moles of water per mole of brexpiprazole, preferably wherein the brexpiprazole is brexpiprazole anhydrate.

3. The crystalline brexpiprazole according to item 1 or 2, wherein the d(90) of the crystalline brexpiprazole is from 40 μm to 100 μm.

4. The crystalline brexpiprazole according to any one of items 1 to 3, wherein the d(10) is from 2.0 μm to 15.0 μm, or from 5 μm to 15 μm, or from 7.5 μm to 15.0 μm.

5. The crystalline brexpiprazole according to any one of items 1 to 4, wherein the d(4,3) is from 15 μm to 90 μm, preferably from 20 μm to 70 μm, from 25 μm to 70 μm, from 25 μm to 60 μm, or from 25 μm to 50 μm.

6. The crystalline brexpiprazole according to any one of items 1 to 5, wherein the particle size distribution of said crystalline brexpiprazole is unimodal.

7. Composition comprising crystalline brexpiprazole according to any one of items 1 to 6.

7a. The crystalline brexpiprazole of any one of items 1 to 6, or the composition of item 7, wherein said crystalline brexpiprazole or composition does not comprise any noticeable amounts of secondary particles.

8. Pharmaceutical composition comprising the crystalline brexpiprazole of any one of items 1 to 6 or the composition according to item 7, and one or more pharmaceutically acceptable excipient.

9. The pharmaceutical composition according to item 8, wherein the one or more pharmaceutically acceptable excipient is selected from the group consisting of inorganic salts, such as sodium chloride;

poloxamers, such as polyoxyethylene(160)polyoxypropylene(30) glycol;

alcohols, such as benzyl alcohol;

benzoic acid esters, such as benzyl benzoate;

bulking agents, such as sugars (e.g. mannitol, lactose, sucrose, trehalose, sorbitol, glucose, raffinose, or a combination thereof), amino acids (e.g. arginine, glycine, or histidine, or a combination thereof), or polymers (e.g. dextran or polyethylene glycol); preferably, the bulking agents are selected from the sugars as listed above, and more preferably, the bulking agents are selected from the group consisting of mannitol, sorbitol, sucrose, or a combination thereof;

viscosity increasing agents, such as dextran, polyvinylpyrrolidone (PVP), gelatine, sodium carboxymethylcellulose (NA CMC), hydroxyethyl starch;

stabilizers, such as antioxidants (e.g. cysteine, ascorbic acid, sodium sulphite, sodiumhydrogensulphite, ethylenediamine tetra acetic acid (EDTA) and preservatives;

isotonizing agents, such as non-electrolytic osmotic modulating agents (e.g. mannitol, sucrose, maltose, xylitol, glucose, starch, sorbitol, glycerol, and propylene glycol); or electrolytic osmotic modulating agents (e.g. sodium chloride, potassium chloride, sodium sulphate, or magnesium chloride); optionally, isotonizing agents can be used singly or in a combination of two or more;

buffers or pH adjusters, such as sodium phosphate, potassium phosphate, tris buffers, sodium hydrogenphosphate, sodium dihydrogenphosphate, trisodium phosphate, and hydrates thereof (e.g. sodium dihydrogenphosphate dihydrate or disodium hydrogenphosphate dodecahydrate); acidic pH adjusters such as hydrochloric acid, acetic acid, or citric acid, or basic pH adjusters such as sodium hydroxide, potassium hydroxide, calcium carbonate, magnesium oxide, or magnesium hydroxide; optionally, the buffers or pH adjusters may be used singly or in a combination of two or more.

10. The pharmaceutical composition according to any one of items 8 to 9, wherein said pharmaceutical composition is in an uncompressed form.

11. The pharmaceutical composition according to any one of items 8 to 10, wherein said pharmaceutical composition is in solid state.

12. The pharmaceutical composition according to item 11, wherein said pharmaceutical composition is a powder.

13. The pharmaceutical composition according to any one of items 8 to 12, not comprising silicone oil or silicone oil derivatives as defined on pages 6 and 7 of WO2012/026562 A1.

14. The pharmaceutical composition according to item 12, wherein the pharmaceutical composition, comprises one or more bulking agents, preferably said bulking agent is mannitol, sorbitol, sucrose, or a combination thereof.

15. The pharmaceutical composition according to item 14, wherein said pharmaceutical composition is suitable for reconstitution to form an aqueous suspension for parenteral administration, preferably for intramuscular or subcutaneous administration, most preferably for intramuscular injection.

16. The pharmaceutical composition according to any one of items 8 to 12, capable of forming an aqueous suspension for parenteral administration, preferably for intramuscular or subcutaneous administration, most preferably for intramuscular injection.

17. Aqueous suspension obtainable or obtained by combining the crystalline brexpiprazole of one of items 1 to 6, or the composition according to item 7, or the pharmaceutical composition of any one of items 8 to 16, with an aqueous solution or water, and optionally further pharmaceutically acceptable excipients.

18. The aqueous suspension according to item 17, wherein the particle size distribution of the crystalline brexpiprazole is as defined in any one of items 1, 3, 4, 5, or 6.

19. Aqueous suspension comprising crystalline brexpiprazole, wherein the crystalline brexpiprazole has a particle size distribution as defined in any one of claims 1, 3, 4, 5, or 6.

20. The aqueous suspension according to any one of items 17 to 19, wherein said crystalline brexpiprazole is combined with water, preferably with water for injection, and optionally further pharmaceutically acceptable excipients.

21. The aqueous suspension according to any one of items 17 to 20, wherein the aqueous suspension is in the form of an injectable preparation, preferably being ready to use.

22. The aqueous suspension according to any one of items 17 to 21, wherein the aqueous suspension is free of noticeable amounts of secondary particles of crystalline brexpiprazole.

Within the meaning of the present invention, there are noticeable amounts of secondary particles present in a sample such as a composition if any of the PSD values (d(90), d(10), and d(4,3)) assessed after the ultrasound treatment of said sample differs by 20% or more, or 10% or more, or 5% or more, from the respective PSD value(s) assessed prior to said ultrasound treatment of said sample.

23. The aqueous suspension according to any one of items 17 to 22, comprising the one or more pharmaceutically acceptable excipients in solid, liquid, or dissolved state.

24. The aqueous suspension according to any one of items 17 to 22, which contains crystalline particles of brexpiprazole as the sole solid species.

25. The aqueous suspension according to any one of items 17 to 24, providing a sustained release of brexpiprazole after administration to a patient, preferably wherein the aqueous suspension maintains a therapeutically effective blood concentration of brexpiprazole for the treatment or prevention of relapse of schizophrenia, bipolar disorder, or depression, for at least one week.

26. The aqueous suspension according to any one of items 17 to 25, comprising the crystalline brexpiprazole in an amount of 0.5 wt.-% to 18.0 wt.-%, preferably 5 wt.-% to 15 wt.-%, based on the total weight of the aqueous suspension.

27. Injectable preparation, comprising the aqueous suspension of any one of items 17 to 26.

28. The injectable preparation according to item 27, consisting of the aqueous suspension of any one of items 17 to 26.

29. The injectable preparation according to item 27 or 28, being ready to use.

30. The injectable preparation according to any one of items 27 to 29, being a sustained-release injectable preparation, preferably maintaining an effective blood concentration of brexpiprazole for the treatment or prevention of relapse of schizophrenia, bipolar disorder, or depression, for at least one week.

31. Vial or prefilled syringe comprising the crystalline brexpiprazole of any one of items 1 to 6, the composition according to item 7, the pharmaceutical composition of any one of items 8 to 16, the aqueous suspension of any one of items 17 to 26, or the injectable preparation of any one of items 27 to 30.

32. The vial or prefilled syringe according to item 31, which provides a unit dose, preferably providing an effective blood concentration of brexpiprazole for the treatment or prevention of relapse of schizophrenia, bipolar disorder, or depression, for at least one week.

33. The vial or prefilled syringe according to item 32, wherein the unit dose provides a unit dose of 10 mg to 90 mg brexpiprazole.

34. Kit including
(a) a vial or prefilled syringe comprising the crystalline brexpiprazole of any one of items 1 to 6, the composition according to item 7 or the pharmaceutical composition of any one of items 8 to 16, and
(b) an aqueous solution or water as defined in item 20.

35. Crystalline brexpiprazole of any one of items 1 to 6, composition according to item 7, pharmaceutical composition of any one of items 8 to 16, aqueous suspension of any one of items 17 to 26, injectable preparation of any one of items 27 to 30, vial or prefilled syringe of any one of items 31 to 33, or kit of item 34, for use in the treatment or prevention of relapse of schizophrenia, bipolar disorder, or depression.

36. Process for the preparation of an aqueous suspension of any one of items 17 to 26, comprising the following steps:
a) Preparing a vehicle, comprising the steps of dissolving one or more of the isotonizing agents, stabilizers, viscosity increasing agents, and bulking agents of item 9 in water, and optionally adjusting the pH by adding buffers or pH adjusters of item 9;
b) optionally, sterilizing the vehicle obtained in step a);
c) incorporating crystalline brexpiprazole having a particle size distribution as defined in any of items 1, 3, 4, 5, or 6, thereby obtaining the aqueous suspension;
d) optionally, carrying out a homogenizing step;
e) optionally, sterilizing the aqueous suspension.

37. The process according to item 36 wherein the aqueous suspension is an injectable preparation of any one of items 27 to 30.

38. Process for the preparation of a vial or prefilled syringe, comprising the process according to item 36 or 37, wherein the process comprises an additional step f) of packaging, e.g. filling the aqueous suspension or injectable preparation into a vial or syringe.

39. Process for the preparation of a lyophilisate comprising the process according to item 36 or 37, wherein the process comprises an additional step f) of freeze drying, thereby obtaining a lyophilisate.

40. The process according to item 39, comprising an additional step g) of packaging, e.g. filling the lyophilisate into a vial or syringe.

41. Use of crystalline brexpiprazole of any one of items 1 to 6, the composition according to item 7, the pharmaceutical composition of any one of items 8 to 16, or the aqueous suspension of any one of items 17 to 26, for the preparation of an injectable preparation of any one of items 27 to 30, or of a vial or prefilled syringe of any one of items 31 to 33.

42. Aqueous suspension comprising anhydrous crystalline brexpiprazole, wherein after 240 minutes at most 15% of brexpiprazole are dissolved, when the dissolution of brexpiprazole is assessed in accordance with the test described in the European Pharmacopoeia, 2.9.3, "Dissolution test for solid dosage forms—Apparatus 4—Flow-through cell" by using a flow through cell with a flow rate of 2 ml/min at a temperature of 37° C., in 0.05M acetate buffer.

43. The aqueous suspension of item 42, wherein the anhydrous crystalline brexpiprazole has a particle size distribution as defined in any one of claims 1, 3, 4, 5, or 6.

Other objects, features, advantages and aspects of the present invention will become apparent to those of skill from the following description. It should be understood, however, that the description and the following specific examples, while indicating preferred embodiments of the invention, are given by way of illustration only. Various changes and modifications within the spirit and scope of the disclosed invention will become readily apparent to those skilled in the art from reading the description and the other parts of the present disclosure.

Definitions

In the context of the present invention the following abbreviations have the indicated meaning, unless explicitly stated otherwise:

| | |
|---|---|
| PSD | Particle Size Distribution |
| PXRD | Powder X-ray diffraction |
| q.s. | "quantum satis" ("sufficient quantity") |

The main characteristics of a PXRD pattern are 2θ(2 Theta)-positions, peak height, peak area and shape (characterized by, for example, peak width or asymmetry, analytical function, empirical representation). In addition to the diffraction peaks, an X-ray diffraction experiment also generates a more-or-less uniform background, upon which the peaks are superimposed. Besides specimen preparation, other factors contribute to the background, for instance the sample holder, diffuse scattering from air and equipment, other instrumental parameters such as detector noise, general radiation from the X-ray tube, etc. The peak-to-background ratio can be increased by minimizing background and by choosing prolonged exposure times. In the context of the present invention, the term "peak" or "reflection" denotes a particular 2-Theta position, wherein the signal-to-noise ratio (calculated according to item 2.2.46 of the European Pharmacopoeia) is at least 3 to 1.

As used herein the term "room temperature" is understood to mean temperatures between 10 and 30° C., typically between 15° C. and 25° C. [see e.g. European Pharmacopoeia 8.3, 1.2 (2015)].

The term "brexpiprazole" means 7-[4-(4-benzo[b]thiophene-4-yl-piperazine-1-yl)butoxy]-1H-quinoline-2-one respectively the compound of Formula I (also referred to herein as "Compound I") itself. "Compound of Formula I" includes an anhydrate of Compound I, a solvate (e.g. a hydrate such as a dihydrate) of Compound I, various crystalline forms of such anhydrates and solvates and mixtures thereof, unless otherwise specified.

Furthermore, unless specified otherwise by the use of a distinct indication, the term "brexpiprazole" used herein means any crystalline form, and any polymorphic form. The skilled person will appreciate that a reference to "brexpiprazole" further defined by powder characteristics, such as particle size parameters, means a reference to a composition consisting of solid brexpiprazole particles having the defined powder characteristics, such as the indicated particle size distribution (PSD).

The term "brexpiprazole dihydrate" as used herein refers to the crystalline form of brexpiprazole disclosed as "dihydrate" in WO 2013/162046 A1 which is characterized by having a PXRD pattern comprising reflections at 2-Theta angles of 8.10, 8.9°, 15.1°, 15.6° and 24.4°, and preferably further peaks at 2-Theta angles of 11.6°, 12.2°, 14.0°, 16.3°, 18.1°, 18.4°, 18.9° and 19.5°, when measured by copper Kalpha$_{1,2}$ radiation through a monochromator at a wavelength of 0.15418 nm. Brexpiprazole dihydrate can have a water content according to Karl Fischer of from 6.5 to 8.8 wt. %.

The term "brexpiprazole anhydrate" as used herein refers to the crystalline form I of brexpiprazole anhydrate, disclosed as "anhydride" in WO 2013/162046 A1, which is characterized by having a PXRD comprising reflections at 2-Theta angles of 6.8°, 10.0°, 10.8°, 14.5°, 14.9°, 17.4°, 19.2°, 20.3°, 21.3° and 23.2° when measured by copper Kalpha$_{1,2}$ radiation through a monochromator at a wavelength of 0.15418 nm. The crystalline form I of brexpiprazole anhydrate can be prepared according to comparative example 1 of WO 2013/162046 A1.

The term "brexpiprazole hydrate" as used herein refers to the crystalline form of brexpiprazole disclosed as "hydrate" in WO 2013/162046 A1 which is characterized by having a PXRD pattern comprising reflections at 2-Theta angles of 7.7°, 9.4°, 11.8°, 18.9° and 24.0°, and preferably further peaks at 2-Theta angles of 5.7°, 8.1°, 8.8°, 10.7°, 12.6°, 13.6°, 13.9°, 15.0°, and 15.6°, when measured by copper Kapha$_{1,2}$ radiation through a monochromator at a wavelength of 0.15418 nm.

For the purpose of this invention, particle size distribution (PSD) is determined as the percent volume at each particle size and measured by a laser diffraction method in the context of a circulating aqueous suspension.

A Malvern Mastersizer 3000 laser diffraction analyzer equipped with a Hydro EV measurement cell was used. About 50 mg of sample were filled into a 15 ml glass test tube. The sample was wetted with two drops of Tween 80 and vortexed. Then the thoroughly wetted sample was dispersed in about 7 mL of UHQ-water by vortexing until the particles were dispersed. The suspension was treated for 7 minutes in an ultrasonification bath at RT (Elma S50H). The well dispersed suspension was then measured in water by adding a sample from the center of the test tube containing the well dispersed suspension to a water-filled dispersion unit prefilled with 70 mL of water. The sample in the 70 mL dispersion unit was kept under stirring at 2000 rpm. More sample from the test tube was added, until a targeted obscuration range of 10-25 percent was achieved. The Malvern Mastersizer was operated using the following parameters:

Background time—8 s.
Measurement time—12 s.
Refractive index dispersant—1.33
Stirring unit—2000 U/min (as mentioned above).
External sonification—5 min (as mentioned above)
Internal sonification—no.
Waiting period—3 Minutes.
Diffraction method—Fraunhofer theory.
Analysis model—general purpose.
Sensitivity—normal
Blue laser was on, results were by volume distribution.

Measurement occurred after an optical alignment of the laser was done and after a background measurement was run. A measurement sequence consisted of eight individual measurements for which the mean value was represented as a histogram.

d90 as used herein means that 90% of the particles (based on volume) are smaller than or equal to the indicated size.

d50 as used herein means that 50% of the particles (based on volume) are smaller than or equal to the indicated size.

d10 as used herein means that 10% of the particles (based on volume) are smaller than or equal to the indicated size.

d(4,3) as used herein denotes the volume mean diameter.

The expression "unimodal particle size distribution" as used herein refers to a particle size distribution with one clear peak. A particle size distribution exhibiting two clear peaks is bimodal.

In general, the term "sustained release" refers to a continuous release of an active pharmaceutical ingredient (API) over an extended period of time after administration of said API, thus providing a prolonged therapeutic effect throughout the release period. In particular, within the meaning of the present invention the term "sustained release" denotes that there is a continuous release of the crystalline brexpiprazole of the present invention after administration thereof to a subject in need thereof (i.e. a patient), to the effect that during a time period of at least one week after administration a therapeutically effective concentration of said brexpiprazole in the blood of the patient is maintained and thus can be determined. The respective blood concentration of brexpiprazole in order to be therapeutically effective may depend on the respective condition that is to be treated (e.g. treatment or prevention of relapse of schizophrenia, bipolar disorder, or depression) and is known to a person skilled in the art.

The term "essentially" used herein means at least 90%, preferably at least 95% and more preferably at least 98% of the indicated reference (e.g. in wt. % if a material is referred to).

The term "burst effect" as used herein means a burst release of API. For a sustained release dosage form, a "burst release" denotes that a large bolus of API is being released before the release rate finally reaches the stable release profile during the sustained release phase. Thus, the burst release usually leads to a higher maximum plasma concentration (c max) when compared to the plasma concentration of the API when a sustained release level has been reached. The burst release usually takes place shortly after administration of a sustained release dosage form. In the pharmacokinetic profile of a sustained release dosage form it can be identified by producing a pronounced peak in the drug's blood level, in case of a sustained release injectable of brexpiprazole in the first week after injection. An example of such a pharmacokinetic behaviour is shown FIG. 15 of CA 02871398.

The term "primary particles" as used herein means individual particles that are not aggregated, but that are separate from each other. Primary particles can occur in different geometrical forms, such as in spherical, cuboidal, or rod-like geometry. Particles without defined geometry are generally referred to as "bulk" or "bulk material".

Primary particles cannot be separated into smaller particles. Secondary particles can be separated in smaller particles by the application of ultrahigh energy (such as ultrasound treatment).

If primary particles agglomerate to larger units, which usually occurs by weak physical interactions such as adhesion, then that are referred to as "agglomerates". These agglomerates are also denoted as "secondary particles". In other words, the term "secondary particles" as used herein refers to primary particles that are agglomerated.

In order to assess whether primary and/or secondary particles are present in a composition, said composition to be tested is subjected to an ultrasound treatment. In a first step, the PSD of the particles that are present the composition is assessed. Then, this composition is subjected to ultrasound treatment, followed by assessing the PSD of the ultrasound-treated composition. A change in PSD is indicative of a change of the particle size of the particles. The change of particle size occurs as due to the ultrasound treatment, existing secondary particles are separated into primary particles.

Within the meaning of the present invention, there are noticeable amounts of secondary particles present in a sample such as a composition if any of the PSD values (d(90), d(10), and d(4,3)) assessed after the ultrasound treatment of said sample differs by 20% or more, or 10% or more, or 5% or more, from the respective PSD value(s) assessed prior to said ultrasound treatment of said sample.

For the purpose of the present invention, assessing whether primary and/or secondary particles are present in a certain composition, the following protocol is applied:

Sample is dispersed in water with addition of Tween 80. The dispersion is treated in an ultrasonic bath for 5 min (for control sample no ultrasonification is performed). Particle size measurement is performed by laser light diffraction (wet measurement) (e.g. Malvern Mastersizer 3000).

The term "therapeutically effective blood concentration" as used herein refers to the concentration of active agent (API; in the present invention, the active agent is brexpiprazole) in the blood, that produces a therapeutic effect.

The term "anhydrous" denotes a substance (e.g. crystalline brexpiprazole) that does not contain substantial amounts of water. An "anhydrate" of a certain substance (e.g. a certain compound, such as crystalline brexpiprazole) defines that said substance has a water content of at most 0.5% according to Karl Fischer.

BRIEF DESCRIPTION OF THE DRAWINGS

FIG. 1: Shows the dissolution profiles of various aqueous suspensions. The x-axis denotes time in minutes, the y-axis the percentage of dissolved brexpiprazole at a given point in time. The dissolution profiles were obtained by the paddle method in 1000 ml at 100 rpm and at pH4.5. The fast onset of dissolution for the "primary particles", with a peak reached after already about 20 minutes is indicative of a burst effect.

DETAILED DESCRIPTION OF THE INVENTION

The invention is described below in further detail by embodiments, without being limited thereto.

In one aspect, the present invention relates to crystalline brexpiprazole exhibiting a specific PSD. It has been surprisingly found by the present inventors that when a crystalline brexpiprazole sample or preparation which, as such and thus in the form of crystalline brexpiprazole particulate material itself, exhibits a PSD of d(90) of 30 μm to 100 μm, d(10) of at least 1.0 μm, and d(4,3) of at least 15.0 μm, is in the form of primary particles and exhibits a dissolution profile that is at least comparable, or even improved when compared to the dissolution profile of prior art brexpiprazole secondary particles.

In particular, it has been surprisingly found that said crystalline brexpiprazole particles, exhibiting the PSD according to the present invention, can prevent or at least minimize the so-called burst effect that can occur in controlled-release formulations such as injectables. The burst release of API can result in drug exposure at undesirable high levels, for example as manifested by blood level peaks potentially resulting in adverse drug effects. Further, a burst release can result in a loss in treatment efficacy, as drug is lost in a comparably uncontrolled and unpredictable pattern. A further reason why a burst effect is not desirable is that the burst effect generally carries the risk of exposing the subject that is provided with the API to a local overdose. Additionally, a burst release is economically inefficient, as a great amount of API is "lost". Further, due to a burst release, the effective lifetime of an API formulation may be shortened.

Without wishing to be bound by any theory, it is assumed that the crystalline brexpiprazole particles according to the present invention having the specific PSD as defined herein minimize or even prevent the formation of secondary particles. It is additionally assumed that this specific PSD, in combination with the minimization or even prevention of the agglomeration of the primary particles to secondary particles, can at least minimize, or even prevent, an undesired burst release of API.

Thus, the present invention relates to crystalline brexpiprazole, wherein the crystalline brexpiprazole has a particle size distribution (PSD) characterized by a d(90) of 30 µm to 100 µm, by a d(10) of at least 1.0 µm, and by a d(4,3) of at least 15.0 µm.

The brexpiprazole can be in the form of an anhydrate, or in the form of a hydrate comprising up to two moles of water per mole of brexpiprazole. In a preferred embodiment, the brexpiprazole is brexpiprazole anhydrate.

The PSD is determined as the percent volume at each particle size and measured by a laser diffraction method in the context of a circulating aqueous suspension.

Alternatively, the PSD can be characterized by a d(90) of crystalline brexpiprazole of 40 µm to 100 µm, and by a d(10) of at least 1.0 µm, and by a d(4,3) of at least 15.0 µm.

Alternatively, the PSD can be characterized by a d(10) of crystalline brexpiprazole of from 2.0 µm to 15.0 µm, or from 5 µm to 15 µm, or from 7.5 µm to 15.0 µm. Additionally, the PSD can further be characterized by a d(90) of 30 µm to 100 µm or of 40 µm to 100 µm, and by a d(4,3) of at least 15.0 µm.

Alternatively, the PSD can be characterized by a d(4,3) from 15 µm to 90 µm, preferably from 20 µm to 70 µm, from 25 µm to 70 µm, from 25 µm to 60 µm, or from 25 µm to 50 µm. Additionally, the PSD can further be characterized by a d(90) of 30 µm to 100 µm or of 40 µm to 100 µm, and by a d(10) of at least 1.0 µm, or of from 2.0 µm to 15.0 µm, or from 5 µm to 15 µm, or from 7.5 µm to 15.0 µm.

The PSD of the crystalline brexpiprazole is determined as disclosed elsewhere herein, by applying a Malvern Mastersizer. A sample of particles that is analysed can exhibit only one maximum, or it can exhibit two or more maxima. A PSD of an analyzed sample of particles showing one maximum, i.e. one clear, distinct peak, is unimodal. This means that most of the particles of the sample exhibit about the same size. A PSD of an analysed sample of particles showing two maxima is bimodal. This means that there are two populations of particles present in the measured sample, with these two populations exhibiting a different size maximum. Thus, dependent on the number of maxima, the PSD is classified as being unimodal, bimodal, or multimodal. In a preferred embodiment of the present invention, the PSD of the crystalline brexpiprazole is unimodal.

In a further aspect, the present invention relates to a composition comprising crystalline brexpiprazole as disclosed herein. Preferably, said composition does not comprise any noticeable amounts of secondary particles. In order to assess whether there are noticeable amounts of secondary particles of crystalline brexpiprazole present, the PSD values (d(90), d(10), d(4,3)) can be assessed prior and after subjecting the composition to ultrasound treatment. If the respectively assessed PSD values differ by 10% or more, or 5% or more, or 3% or more, it is concluded that there are noticeable amounts of secondary particles present.

Likewise, as described above for the crystalline brexpiprazole particles having the specified PSD themselves, the absence of noticeable amounts of secondary particles in the composition can at least further contribute to improved properties of crystalline brexpiprazole, such as with regard to dissolution profile (minimizing or even avoiding burst release), or with regard to processability (formulating final dosage forms).

In a further aspect, the present invention refers to a pharmaceutical composition that comprises the crystalline brexpiprazole of the present invention, and to a composition that that comprises the crystalline brexpiprazole of the present invention. It is preferred that neither the pharmaceutical composition nor the composition comprise noticeable amounts of secondary particles thereof. In other words, the composition and the pharmaceutical composition of the present invention comprise crystalline brexpiprazole essentially, preferably exclusively, in form of primary particles.

Said pharmaceutical composition and said composition additionally comprise one or more pharmaceutically acceptable excipient(s).

Preferably, this pharmaceutically acceptable excipient is suitably one or more selected from the group consisting of inorganic salts, such as sodium chloride;

poloxamers, such as polyoxyethylene(160)polyoxypropylene(30) glycol;

alcohols, such as benzyl alcohol;

benzoic acid esters, such as benzyl benzoate;

bulking agents, such as sugars (e.g. mannitol, lactose, sucrose, trehalose, sorbitol, glucose, raffinose, or a combination thereof), amino acids (e.g. arginine, glycine, or histidine, or a combination thereof), or polymers (e.g. dextran or polyethylene glycol); preferably, the bulking agents are selected from the sugars as listed above, and more preferably, the bulking agents are selected from the group consisting of mannitol, sorbitol, sucrose, or a combination thereof;

viscosity increasing agents, such as dextran, polyvinylpyrrolidone (PVP), gelatine, sodium carboxymethylcellulose, hydroxyethyl starch;

stabilizers, such as antioxidants (e.g. cysteine, ascorbic acid, sodium sulphite, sodiumhydrogensulphite, ethylenediamine tetra acetic acid (EDTA) and preservatives;

isotonizing agents, such as non-electrolytic osmotic modulating agents (e.g. mannitol, sucrose, maltose, xylitol, glucose, starch, sorbitol, glycerol, and propylene glycol); or electrolytic osmotic modulating agents (e.g. sodium chloride, potassium chloride, sodium sulphate, or magnesium chloride); optionally, isotonizing agents can be used singly or in a combination of two or more;

buffers or pH adjusters, such as sodium phosphate, potassium phosphate, tris buffers, sodium hydrogenphosphate, sodium dihydrogenphosphate, trisodium phosphate, and hydrates thereof (e.g. sodium dihydrogenphosphate dihydrate or disodium hydrogenphosphate dodecahydrate); acidic pH adjusters such as hydrochloric acid, acetic acid, or citric acid, or basic pH adjusters such as sodium hydroxide, potassium hydroxide, calcium carbonate, magnesium oxide, or magnesium hydroxide; optionally, the buffers or pH adjusters may be used singly or in a combination of two or more.

The pharmaceutical composition can be present in various forms, such as in an uncompressed form. Suitable uncompressed forms are known to a person skilled in the art.

Examples of such suitable uncompressed forms are a liquid, e.g. a suspension, or a powder.

The choice of pharmaceutically acceptable excipient(s) that is (are) present in the pharmaceutical composition is also dependent on the respective form (or state) of said composition. For instance, if the pharmaceutical composition is intended to be in form of a powder, a person skilled in the art will choose the pharmaceutically acceptable excipients that are suitable for this purpose.

Alternatively, or additionally, the pharmaceutical composition can be present in solid state. This solid state can be an uncompressed or a compressed solid state. Dependent on whether compression is carried out, excipients may have to be present that render the pharmaceutical composition compressible.

Examples of pharmaceutical compositions in solid state are tablets, capsules, powders, or lozenges. Of these, tablets are an example of a compressed, solid form.

Particular examples of pharmaceutical compositions in uncompressed solid forms are powders, capsules, and lyophilisates.

A "lyophilisate" is the result of a process called lyophilisation. Lyophilization, also referred to as "freeze drying", is a process in which water or another solvent is frozen, followed by the removal of said water/solvent from the sample, by sublimation and then by desorption. During lyophilization, the moisture content of the sample is reduced to such a low level that for instance does not support chemical reactions. Lyophilization thus is particularly useful in formulating APIs that are thermolabile and/or unstable in water.

It is known to a person skilled in the art that different formulation techniques may require specific pharmaceutically acceptable excipients, dependent on the respective demands of the applied technique(s) and/or the envisaged final product or final dosage form, respectively. For instance, if a lyophilisate shall be prepared, it is one important aspect to provide a lyophilisate that can be reconstituted without any problems. Therefore, excipients have to be added that provide for an adequate structure to the lyophilisate, with this adequate structure allowing a proper reconstitution. Accordingly, if the pharmaceutical composition of the present invention is in form of a lyophilisate, one or more bulking agents, such as sugars (e.g. mannitol, lactose, sucrose, trehalose, sorbitol, glucose, raffinose, or a combination thereof), amino acids (e.g. arginine, glycine, or histidine, or a combination thereof), or polymers (e.g. dextran or polyethylene glycol), are preferably present. In a more preferred embodiment, said bulking agent(s) is (are) mannitol, sorbitol, sucrose, or a combination thereof. Bulking agents, and in particular the above bulking agents, provide for a proper structure of the lyophilizate (cake).

The pharmaceutical composition of the present invention, being in form of a lyophilisate, is suitable for reconstitution to form an aqueous suspension for parenteral administration, preferably for intramuscular or subcutaneous administration, most preferably for intramuscular injection.

Reconstitution can for instance be carried out by adding a suitable aqueous solution, preferably water for injection, to the lyophilisate.

In a further aspect, the pharmaceutical composition of the present invention that is not in form of a lyophilisate, is capable of forming an aqueous suspension for parenteral administration, preferably for intramuscular or subcutaneous administration, most preferred for intramuscular injection.

Upon reconstitution of said pharmaceutical composition that is suitable for reconstitution, or of said pharmaceutical composition that is capable of forming an aqueous suspension for parenteral administration, with an aqueous solution or water for injection, an aqueous suspension is obtained. In an optional embodiment, additionally further pharmaceutically acceptable excipients can be added.

Thus, in a further aspect the present invention relates to an aqueous suspension obtainable or obtained by combining the crystalline brexpiprazole of the present invention, or the composition of the present invention, or the pharmaceutical composition according to the present invention, with an aqueous solution or water. Optionally, further pharmaceutically acceptable excipient(s) is (are) added.

In a preferred aspect, said crystalline brexpiprazole as defined in the present invention, being present in an aqueous suspension, is combined with water, preferably with water for injection, and optionally further pharmaceutically acceptable excipients.

In a further preferred aspect, said aqueous solution preferably has a pH value of 4 to 9, more preferably 5 to 8, even more preferred of 6.0 to 7.5.

It is additionally preferred that said aqueous suspension comprises crystalline brexpiprazole having a PSD characterized by a d(90) of 30 µm to 100 µm, by a d(10) of at least 1.0 µm, and by a d(4,3) of at least 15.0 µm.

Alternatively, said aqueous suspension comprises crystalline brexpiprazole having a PSD characterized by a d(90) of crystalline brexpiprazole of 40 µm to 100 µm, and by a d(10) of at least 1.0 µm, and by a d(4,3) of at least 15.0 µm.

Alternatively said aqueous suspension comprises crystalline brexpiprazole having a PSD characterized by a d(10) of crystalline brexpiprazole of from 2.0 µm to 15.0 µm, or from 5 µm to 15 µm, or from 7.5 µm to 15.0 µm. Additionally, the PSD can further be characterized by a d(90) of 30 µm to 100 µm or of 40 µm to 100 µm, and by a d(4,3) of at least 15.0 µm.

Alternatively, said aqueous suspension comprises crystalline brexpiprazole having a PSD characterized by a d(4,3) from 15 µm to 90 µm, preferably from 20 µm to 70 µm, from 25 µm to 70 µm, from 25 µm to 60 µm, or from 25 µm to 50 µm. Additionally, the PSD can further be characterized by a d(90) of 30 µm to 100 µm or of 40 µm to 100 µm, and by a d(10) of at least 1.0 µm, or of from 2.0 µm to 15.0 µm, or from 5 µm to 15 µm, or from 7.5 µm to 15.0 µm.

The present invention further relates to an aqueous suspension comprising crystalline brexpiprazole having a PSD characterized by a d(90) of 30 µm to 100 µm, by a d(10) of at least 1.0 µm, and by a d(4,3) of at least 15.0 µm, and optionally additionally one or more pharmaceutically acceptable excipient(s).

Alternatively, said aqueous suspension comprises crystalline brexpiprazole having a PSD characterized by a d(90) of crystalline brexpiprazole of 40 µm to 100 µm, and by a d(10) of at least 1.0 µm, and by a d(4,3) of at least 15.0 µm.

Alternatively said aqueous suspension comprises crystalline brexpiprazole having a PSD characterized by a d(10) of crystalline brexpiprazole of from 2.0 µm to 15.0 µm, or from 5 µm to 15 µm, or from 7.5 µm to 15.0 µm. Additionally, the PSD can further be characterized by a d(90) of 30 µm to 100 µm or of 40 µm to 100 µm, and by a d(4,3) of at least 15.0 µm.

Alternatively, said aqueous suspension comprises crystalline brexpiprazole having a PSD characterized by a d(4,3) from 15 µm to 90 µm, preferably from 20 µm to 70 µm, from 25 µm to 70 µm, from 25 µm to 60 µm, or from 25 µm to 50 µm. Additionally, the PSD can further be characterized by a d(90) of 30 µm to 100 µm or of 40 µm to 100 µm, and by a d(10) of at least 1.0 µm, or of from 2.0 µm to 15.0 µm, or from 5 µm to 15 µm, or from 7.5 µm to 15.0 µm.

As described above, it is possible that, in one embodiment, said aqueous suspensions additionally comprise pharmaceutically acceptable excipients.

The concentration of the pharmaceutical acceptable excipients contained in the aqueous suspension may vary depending on the type of pharmaceutical acceptable excipients. For example, the one or more pharmaceutically acceptable excipients are contained in the aqueous suspension, in particular injectable preparation, in a concentration of about 0.01 mg/ml to 500.00 mg/ml, more preferably about 0.05 mg/ml to 450.00 mg/ml, and even more preferably about 0.06 mg/ml to 300.00 mg/ml. The one or more pharmaceutically acceptable excipients is preferably contained in an amount of about 0.01 parts by weight to 500.00 parts by weight, more preferably about 0.05 parts by weight to 450.00 parts by weight, and even more preferably about 0.06 parts by weight to 300.00 parts by weight, per 100 parts by weight of brexpiprazole.

This one or more pharmaceutically acceptable excipient(s) can be present in said aqueous suspensions in solid, liquid, or dissolved state.

It is however preferred that the crystalline particles of brexpiprazole are the sole solid species in the aqueous suspensions. In other words, the pharmaceutically acceptable excipient(s) that can optionally be present are present in dissolved state, if present.

In a further preferred embodiment, the aqueous suspensions comprise the crystalline brexpiprazole in an amount of 0.5 wt.-% to 18.0 wt.-%, preferably 5 wt.-% to 15 wt.-%, based on the total weight of the aqueous suspension.

In an additionally preferred embodiment, the aqueous suspensions of the present invention comprising crystalline brexpiprazole having a PSD as defined herein, are free of any noticeable amounts of secondary particles of crystalline brexpiprazole.

Alternatively, or additionally, the aqueous suspensions are redispersible.

In a further preferred embodiment, said aqueous suspensions are in the form of a sterile injectable preparation, with this sterile injectable preparation preferably being ready to use.

Within the meaning of the present invention, the expression "ready to use" means that said suspension can be used for administration immediately, with no need to subject said suspension to further preparation steps or the like, such as a lyophilisation and/or reconstitution step.

As is known to a person skilled in the art, in general, brexpiprazole is used in treating central nervous system diseases, such as schizophrenia. In such diseases, a long-acting medication administration form is useful, because it increases patients' compliance, thereby lowering the relapse rate during treatment.

It is thus preferred that the aqueous suspensions of the present invention provide a sustained release of brexpiprazole after administration to a patient, preferably wherein the aqueous suspensions maintain an effective blood concentration of brexpiprazole for the treatment or prevention of relapse of schizophrenia, bipolar disorder, or depression, for at least one week.

It is particularly preferred that said aqueous suspensions are ready to use for parenteral administration, e.g. without the aqueous suspensions being firstly lyophilized and subsequently reconstituted.

In a further aspect, the present invention relates to an injectable preparation, preferably sterile injectable preparation, comprising the aqueous suspensions of the present invention. In a preferred embodiment, the injectable preparation consists of said aqueous suspensions. It is further preferred that the injectable preparation, comprising or consisting of the aqueous suspensions, is ready to use.

As maintaining an effective blood concentration of brexpiprazole for at least one week is useful, it is preferred that the injectable preparation is a sustained-release injectable preparation, preferably maintaining an effective blood concentration of brexpiprazole for the treatment or prevention of relapse of schizophrenia, bipolar disorder, or depression, for at least one week.

In a further aspect, the present invention relates to a vial or prefilled syringe containing the crystalline brexpiprazole according to the present invention, the composition according to the present invention, the pharmaceutical composition of the present invention, the aqueous suspension according to the present invention, or the injectable preparation according to the present invention.

In a preferred embodiment, the vial or prefilled syringe provides a unit dose, preferably providing an effective blood concentration of brexpiprazole for the treatment or prevention of relapse of schizophrenia, bipolar disorder, or depression, for at least one week.

In an additional preferred embodiment, the unit dose provides a unit dose of 10 mg to 90 mg brexpiprazole.

In a further aspect, the present invention relates to a kit including
(a) a vial or prefilled syringe comprising the crystalline brexpiprazole, the composition or the pharmaceutical composition, respectively according to the present invention, and
(b) an aqueous solution or water according to the present invention.

In a preferred embodiment, the vial or prefilled syringe of component (a) of the kit comprises the crystalline brexpiprazole, the composition or the pharmaceutical composition in lyophilized form, i.e. as freeze-dried product.

In a further preferred embodiment, and in particular preferred if compound (a) is a freeze-dried product, component (b) of the kit is water for injection. This water for injection can be used for reconstitution at the time of use.

In a further aspect, the present invention refers to crystalline brexpiprazole, composition, pharmaceutical composition, aqueous suspension, injectable preparation, vial or prefilled syringe, or kit, respectively according to the present invention, for use in the treatment or prevention of relapse of schizophrenia, bipolar disorder, or depression.

In a further aspect, the present invention also refers to a process for the preparation of the aqueous suspension as disclosed herein. The process comprises the steps of
a) preparing a vehicle, comprising the steps of dissolving one or more of the isotonizing agents, stabilizers, viscosity increasing agents, and bulking agents as disclosed herein in aqueous solution or water, preferably water, and optionally adjusting the pH by adding buffers or pH adjusters as disclosed herein;
b) optionally, sterilizing the vehicle obtained in step a);
c) incorporating crystalline brexpiprazole, preferably sterile crystalline brexpiprazole, having a particle size distribution as disclosed herein, thereby obtaining the aqueous suspension;
d) optionally, carrying out a homogenizing step; and
e) optionally, sterilizing the aqueous suspension.

In step a), a vehicle is prepared. In general, a vehicle is a substance, usually without therapeutic action, that is used as a medium to give bulk for the administration of medicines.

In the present invention, the vehicle is prepared by dissolving one or more of the isotonizing agents, stabilizers, viscosity increasing agents, and bulking agents, as disclosed herein, in an aqueous solution or water, preferably in water, and optionally the pH is adjusted by adding buffers or pH adjusters. In a preferred embodiment, as viscosity increasing agent Na CMC is used, as bulking agent mannitol is used, and as buffer or pH adjuster sodium dihydrogenphosphate and sodium hydroxide (NaOH) are used.

The vehicle in step a) can be prepared in a sterile manner or in an unsterile manner. In a preferred embodiment, the vehicle in step a) is prepared in an unsterile manner.

If a step of adjusting the pH is carried out, then in a preferred embodiment, the pH is adjusted to a pH value of 4 to 9, more preferably of 5 to 8, and even more preferably of 6.0 to 7.5. It is particularly preferred that the pH as a value of about 7.

In an optional step b), the vehicle obtained in step a) is sterilized. This sterilization step can be carried out by any suitable sterilization method that is known to a person skilled in the art, such as by autoclaving, sterile filtration, etc., after being prepared. It is preferred that, if the optional step b) is carried out, the vehicle is sterile filtrated.

If the vehicle of step a) is prepared in an unsterile manner, then it is preferred that step b) is carried out.

In step c), the crystalline brexpiprazole having the PSD as disclosed herein is incorporated into the vehicle obtained in step a). The incorporation of the API is carried out as known to a person skilled in the art for suspension systems: Preferably the API is slowly added to the vehicle under continuos stirring (vessel with a suitable mixing device). As a result, an aqueous suspension is obtained.

In one embodiment, the crystalline brexpiprazole that is used for preparing the aqueous suspension is sterile. In order to obtain sterile crystalline brexpiprazole, one or more of the following methods can be applied: sterilization by means of ionizing irradiation with an electron beam or gamma rays, aseptic crystallization, UV irradiation, autoclaving, and the like.

As a result of steps a) to c), an aqueous suspension is obtained, with this aqueous suspension comprising the crystalline brexpiprazole exhibiting the PSD as disclosed herein, and one or more of the isotonizing agents, stabilizers, viscosity increasing agents, and bulking agents as disclosed herein.

As an optional step d), a homogenizing step can be carried out. The homogenization is carried out by any suitable means that is known to a person skilled in the art. As a result, this homogenization step improves homogeneous distribution of the API. In a preferred embodiment, homogenization is preferably performed by using a flow-through homogenization unit.

Finally, an optional step e) of sterilizing the aqueous suspension can be carried out. This optional step is of particular importance if during the previous steps a) to d) no sterilization step has been carried out, or if none of the used components was sterile.

This sterilization step e) can be carried out by applying any suitable method that is known to a person skilled in the art. Preferably, sterilization is carried out as described in and according to the EMA Guidelines (European Medicines Agency, 11 Aug. 2016, "Guidelines on the sterilisation of the medicinal product, active substance, excipient and primary container"). The sterilization techniques described therein are steam sterilisation, dry heat sterilization, ionization radiation sterilization and gas sterilization.

In a preferred embodiment, the process for the preparation of an aqueous suspension comprises, more preferably consists of, the following steps:
a) preparing the vehicle as disclosed above, wherein the vehicle is unsterile;
b) sterilizing the vehicle obtained in step a), preferably by carrying out a sterilfiltration step; and
c) incorporating the crystalline brexpiprazole, with this crystalline brexpiraziole being sterile.

In a preferred embodiment, the aqueous suspension prepared according to the process according to the present invention is an injectable preparation as disclosed herein.

In a further embodiment, additional steps can be carried out after step c) (if optional steps d) and e) are not carried out), after step d) (if this optional step is carried out and if step e) is not carried out), or after step e) (if optional step d) is carried out).

One example of such an additional step is a step f) of packaging the obtained aqueous suspension or injectable preparation into a vial or syringe. Preferably, packaging step f) is a filling step.

Another example of such an additional step is a step of formulating the aqueous suspension into a lyophilizate (freeze-dried product). In this case, the additional step f) is a freeze-drying step. In a preferred embodiment, a freeze-drying step comprises a freezing step, and a primary and secondary drying step.

The thus-obtained lyophilizate (freeze-dried product) can then be packaged into a vial or syringe. The lyophilizate can be formulated into an injectable preparation by the addition of water for injection at the time of use.

The present invention also refers to the use of crystalline brexpiprazole, the composition, the pharmaceutical composition, or the aqueous suspension, respectively as disclosed herein, for the preparation of an injectable preparation or of a vial or of a prefilled syringe, respectively as disclosed herein.

The present invention also refers to an aqueous suspension comprising anhydrous crystalline brexpiprazole, wherein after 240 minutes at most 15% of brexpiprazole is dissolved, when the dissolution of brexpiprazole is assessed in accordance with the test described in the European Pharmacopoeia, 2.9.3, "Dissolution test for solid dosage forms"—Apparatus 4 (Flow-through cell), with the following modifications: a flow through cell according to the Pharmacopoeia with 12 mm dimensions was used with a flow rate of 2 ml/min in 0.05M acetate buffer at pH 4.5 and 22° C. A small cell was used, and was filled to 50% of the cell height with 1 mm glass beads. A glass microfiber filter, grade GF/D, was put on top of the glass beads. The 100 µl sample was then charged on top of the filter on the glass beads and then the remainder of the cell was filled with more glass beads. A peristaltic-pump by Ismatec of type "Reglo ICC" was used with an inert tubing. 10 ml fractions were collected to represent 5 min intervals. In a preferred embodiment, the anhydrous crystalline brexpiprazole has a PSD as disclosed herein.

Finally, the present invention also refers to an aqueous suspension comprising anhydrous crystalline brexpiprazole, wherein after 10 minutes at most 60% of brexpiprazole is dissolved, when the dissolution of brexpiprazole is assessed in accordance with the test described in the European Pharmacopoeia, 2.9.3, "Dissolution test for solid dosage forms"—Apparatus 2 (Paddle apparatus)." by using a paddle apparatus with a volume of 1000 ml at a temperature of 37°

C., in 0.05M acetate buffer, pH4.5 at 50 rpm, such as a Sotax Smart AT 7. In a preferred embodiment, the anhydrous crystalline brexpiprazole has a PSD as disclosed herein.

The present inventors have also identified a second and separate concept for the preparation of an injectable preparation exhibiting improved performance, for example with regard to processability and/or dissolution profile, wherein said second formulation is easy to prepare and/or are less likely to cause allergic reactions. The following pages until page 25 relate to this second inventive concept.

It was surprisingly found that when an oily suspension of crystalline brexpiprazole is selected for a brexpiprazole-containing composition, such compositions (for instance pharmaceutical compositions such as injectables) that comprise crystalline brexpiprazole as a suspension in oil exhibit a dissolution profile wherein release is more strongly delayed when compared to, the dissolution profile of comparative prior art compositions (such as comparative injectables) comprising secondary particles of crystalline brexpiprazole. For instance, it was beneficially found in the present invention that a burst effect, i.e. an initial release of brexpiprazole leading to undesired blood levels, can be avoided. Moreover, pharmaceutical compositions, such as injectable preparations, comprising the crystalline brexpiprazole as an oily suspension are advantageous with regard to processability.

Moreover, since an oily suspension comprising crystalline brexpiprazole exhibits an acceptable or even improved dissolution profile, it is not necessary anymore to provide secondary particles of brexpiprazole, as it is the case in prior art. This enables improved processability and applying simpler formulation techniques: no time-consuming, costly measures, such as the addition of specific excipients that promote aggregation of brexpiprazole primary particles, have to be taken that would otherwise be necessary to obtain the conventionally sought secondary particles. This for instance additionally creates the possibility of formulating said crystalline brexpiprazole in dosage forms, such as injectables, without adding aggregation-promoters such as binders. In other words, by the provision and the use of oily suspensions of crystalline brexpiprazoleas defined herein, addition of certain excipients can be avoided, thereby minimizing the exposure of patients to potential allergens. At the same time a burst effect of an injectable oily suspension comprising crystalline brexpiprazole can be avoided.

Accordingly, the present invention provides a second inventive concept providing the following aspects, subject-matter and preferred embodiments which, respectively taken alone or in combination, contribute to providing improved technical effects and to solving the afore-mentioned object of the invention:

II.1. Pharmaceutical composition comprising brexpiprazole, characterized in that it is a suspension wherein the active ingredient brexpiprazole is suspended, essentially in its solid phase, in an anhydrous liquid vehicle.

II.2. Pharmaceutical composition according to item II.1, wherein brexpiprazole is in crystalline form.

II.3. Pharmaceutical composition according to any one of the preceding items, characterized in that it is an oily suspension.

II.4. Pharmaceutical composition according to any one of the preceding items, said pharmaceutical composition being an oily suspension wherein the continuous phase consists essentially of polyol fatty acid esters.

II.5. Pharmaceutical composition according to any one of items II.3 to II.4, wherein the continuous phase consists essentially of polyol fatty acid esters containing fatty acids with a chain length of 6 to 22 C-atoms.

II.6. Pharmaceutical composition according to any one of items II.3 to II.5, wherein the continuous phase consists essentially of glycerol fatty acid esters containing fatty acids with a chain length of 6 to 22 C-atoms.

II.7. Pharmaceutical composition of item II.6, wherein the fatty acids have a chain length of 16 to 20 C-atoms.

II.8. Pharmaceutical composition according to any one of items II.3 to II.7, wherein the continuous phase consists essentially of plant oils.

II.9. Pharmaceutical composition of item II.8, wherein the plant oil is selected from the group consisting of sesame oil, peanut oil, corn oil and castor oil.

II.10. Pharmaceutical composition according to any one of items II.3 to II.7, further characterized in that the pharmaceutical composition additionally comprises a wetting agent.

II.11. Pharmaceutical composition according to any one of items II.2 to II.13, wherein the crystalline brexpiprazole is brexpiprazole anhydrate.

II.12. Pharmaceutical composition according to any one of items II.2 to II.11, wherein the crystalline brexpiprazole is characterized by having a particle size distribution (PSD) characterized by a d(90) of 5 μm to 90 μm, preferably by a d(90) of 10 μm to 50 μm.

II.13. Pharmaceutical composition according to any one of items II.2 to II.12, wherein the particle size distribution of said crystalline brexpiprazole is unimodal.

II.14. Pharmaceutical composition according to any one of items II.2 to II.13, wherein said composition does not comprise any noticeable amounts of secondary particles.

II.15. Pharmaceutical composition according to any one of items II.2 to II.14, wherein at least 50 mg and at most 150 mg crystalline brexpiprazole are present per 1.0 ml of suspension.

II.16. Pharmaceutical composition of item II.15, wherein at least 80 mg and at most 120 mg crystalline brexpiprazole are present per 1.0 ml of suspension II.17. Pharmaceutical composition as in any one of the preceding items for subcutaneous or intramuscular administration.

II.18. Pharmaceutical composition as in one of the preceding items for the treatment or prevention of schizophrenia, bipolar disorder, or depression.

II.19. Use of crystalline brexpiprazole anhydrate for the preparation of a medicament which can be sterilized by heat.

II.20. Use according to item II-19, wherein, when the medicament is heated to 121° C. over 20 minutes at 0.2 mPa, less than 1% of brexpiprazole decomposes.

II.21. Process for the production of a sterile pharmaceutical composition containing crystalline brexpiprazole anhydrate, comprising the step of autoclaving of a pharmaceutical composition containing crystalline brexpiprazole anhydrate.

II.22. Kit for the treatment or prevention of schizophrenia, bipolar disorder, or depression, comprising
  (a) a pharmaceutical composition according to any one of the preceding items
  (b) an injection device.

This invention therefore also relates to pharmaceutical compositions comprising brexpiprazole, wherein the pharmaceutical composition is a suspension of brexpiprazole in solid form suspended in an anhydrous liquid vehicle.

The suspension is preferably an oily suspension. In that suspension the brexpiprazole is suspended, essentially in its solid phase, in a liquid vehicle which is not water.

For the purpose of this patent application, the expression "essentially" means over 90 percent of brexpiprazole present in the solid state. Preferably brexpiprazole is contained, in its solid phase, at over 95 percent, and especially at over 97 percent or over 99 percent based on the weight of all brexpiprazole present in the composition.

For the pharmaceutical compositions of this second inventive concept herein, the term "oily suspension" refers to a dispersion in which the continuous phase (the "vehicle") is contained in the form of a liquid lipid, while the term "solid phase" refers to the presence of brexpiprazole as a solid form. The brexpiprazole can, for example, be present in the form of crystalline particles or amorphous particles, or it may be bound to a suitable carrier material such as excipient microparticles.

In a preferred embodiment the brexpiprazole is largely insoluble in the anhydrous liquid vehicle. This leads to a protracted release of brexpiprazole from its solid phase after the suspension is injected into a subject to be treated, for example by way of an intramuscular injection.

The expression "largely insoluble in the anhydrous liquid vehicle" is to be interpreted in that at room temperature at most 10 percent of brexpiprazole is dissolved in the liquid vehicle. Preferred are anhydrous liquid vehicles in which brexpiprazole is soluble at at most 5 percent, such as at most 3 percent or even at most 1 percent.

Therefore, it is preferred that the pharmaceutical composition comprising brexpiprazole is anhydrous. For the pharmaceutical compositions of this second inventive concept herein, the term "anhydrous" is to be interpreted as referring to a water content of at most 3 percent, such as at most 1 percent and preferably at most 0.5 percent.

When a pharmaceutical composition according to this second inventive concept herein is administered, the brexpiprazole is continually released from its solid phase over an extended period of time without showing a burst effect so that a therapeutically effective plasma level can be obtained over a period of at least 7 days, preferably more than 14 days and most desirably more than 28 days. As an advantageous result, the frequency of brexpiprazole administration can be reduced to one single application per week or every two or three weeks.

In the suspension brexpiprazole can be present as a highly water-soluble, pharmaceutically acceptable salt that is not or only weakly soluble in aliphatic solvents and especially oils and is thus largely insoluble in a corresponding anhydrous formulation.

Preferably brexpiprazole is present as its free form and preferably in crystalline free form, such as crystalline brexpiprazole dihydrate or brexpiprazole anhydrate. Preferably brexpiprazole is present as crystalline brexpiprazole anhydrate.

The range of the Brexpiprazole concentration in the suspension is for example at least 50 mg and at most 150 mg brexpiprazole per 1.0 ml of suspension, such as at least 80 mg and at most 120 mg brexpiprazole.

It is preferred that the crystalline brexpiprazole has a particle size distribution (PSD) characterized by a d(90) of 5 μm to 90 μm, preferably by a d(90) of 10 μm to 50 μm.

Suitable amounts of brexpiprazole per single injection may be 30 mg to 70 mg, such as at least 40 mg to at most 60 mg, for example 50 mg per single injection.

A pharmaceutical composition according to this second inventive concept herein may be based for instance on a continuous phase consisting of a pharmaceutically acceptable oil, such as liquid glycerol-based fatty acid esters, lipidols or aliphatic hydrocarbons (e.g. paraffin), in which the brexpiprazole is present in solid form, for example in the form of crystalline brexpiprazole anhydrate. From this lipid-containing or hydrophobic phase the brexpiprazole, when administered to the patient by intramuscular injection, will be released only slowly.

A preferred oily suspension of the invention that contains brexpiprazole in its solid phase is a suspension wherein the continuous phase is a lipid.

Pharmaceutically acceptable lipids include for example vegetable oils such as almond oil, olive oil, poppy oil, peanut oil or sesame oil, higher-level fatty acids such as oleic acid, as well as fatty-acid mono-, di- or tri-esters from mono- or polyols such as isopropanol, 1,3-propanediol, glycerol, 1,2-butanediol or 1,2,3-butanetriol. Preferred is an oily suspension wherein the vehicle essentially consists of polyol fatty acid esters. The term "polyol fatty acid esters" also includes mixtures of various polyol fatty acid esters.

Preferred polyols for the polyol component of the polyol fatty acid esters are polyols with two to four C-atoms and a variable number of hydroxy groups, such as 1,3-propanediol, glycerol, 1,2,3-butanetriol, 1,2,4-butanetriol or 1,3-butanediol, with glycerol being particularly preferred.

The overall esterification level of the polyol fatty acid esters of the continuous phase is preferably 80-100 percent and ideally 90-100 percent. The preferred chain length of the fatty acids in said polyol fatty acid esters of the vehicle is between 6 and 22 C-atoms and more preferably between 16 and 20 C-atoms.

The proportional amount of the continuous phase (of the vehicle) in the pharmaceutical composition of this second inventive concept herein is a function of the concentrations of the active agent and any other optional adjuvants. It is typically at least 75 percent, preferably from 80 percent to 98 percent, and in particular it is at least 85 percent and at most 95 percent by weight based on the total weight of the suspension.

The pharmaceutical composition according to this second inventive concept herein may optionally also contain a wetting agent. The term "wetting agent" refers to a substance that reduces the interfacial tension between the surface of the vehicle and that of the active agent. For example the wetting agent could be glycerol monocaprylate.

If present, the optional wetting agent may be present at a concentration (in w/w) of at most 2.5 percent, such as at most 1.0%.

The pharmaceutical composition according to this second inventive concept herein may also contain additives and adjuvants such as a lipid-soluble antioxidant, e.g. vitamin E. This addition will stabilize compositions comprising for example unsaturated fatty acids.

The pharmaceutical composition according to this second inventive concept herein can be produced in particularly simple and practical fashion by suspending solid brexpiprazole in a liquid, oily phase. The vehicle used for the oily phase and the optional further ingredients are as described above. Preferably the brexpiprazole is used in the crystalline state and especially as crystalline brexpiprazole anhydrate, and the composition is produced without the addition of water.

The following are concentrations (in w/w) which may be used for the production of the oily suspension according to the second concept of this invention: 1-20 percent brexpiprazole, preferably 2-18 percent and in particular 4-15 percent; for the anhydrous vehicle, 77.5-99 percent, preferably 79.5-98 percent and in particular 82.5-96 percent; and optionally wetting agent to at most 2.5%. The oily suspensions may be sterilized, e.g. by autoclaving.

The oily suspensions are suited to administration by injection. The injection is preferably an intramuscular injection.

The present invention is illustrated in the following examples, which should not be construed as limiting.

EXAMPLES

Particle Size Distribution

Particle size distribution was measured with a Malvern Mastersizer 3000 laser diffraction analyzer equipped with a Hydro EV measurement cell. About 50 mg of sample were given into a test tube. The sample was wetted with two drops of Tween 80 and dispersed in about 7 ml of water on a Vortexer. The suspension was treated for 7 minutes in a ultrasonification bath (Elma S50H). The well dispersed suspension was afterwards measured in water at a targeted obscuration range of 10-25 percent while circulating the aqueous suspension and stirring the suspension reservoir at 2000 rpm after a waiting period of three minutes. A fraunhofer optical model was utilized to deconvolute the sample scattering patterns to yield the resultant particle size distributions. Analysis model: General purpose/normal sensitivity. Measuring/background time: about 10 sec Dissolution Profile In some experiments the dissolution profile was determined according to Ph. Eur. 2.9.3 Dissolution test for solid dosage forms Apparatus 4 (Flow-through cell) with modifications. Dissolution was carried out by using a flow-through cell (powder cell), flow 0.5 ml/min, 0.05M Acetate buffer pH 4.5.

The dissolution of brexpiprazole was assessed in accordance with the test described in the European Pharmacopoeia, 2.9.3, "Dissolution test for solid dosage forms"—Apparatus 4 (Flow-through cell), with the following modifications: a flow through cell according to the Pharmacopoeia with 12 mm dimensions was used with a flow rate of 2 ml/min in 0.05M acetate buffer at pH 4.5 and 22° C. A small cell was used, and was filled to 50% of the cell height with 1 mm glass beads. A glass microfiber filter, grade GF/D, was put on top of the glass beads. The 100 μl sample was then charged on top of the filter on the glass beads and then the remainder of the cell was filled with more glass beads. A peristaltic-pump by Ismatec of type "Reglo ICC" was used with an inert tubing. 10 ml fractions were collected to represent 5 min intervals.

Where indicated, the dissolution profile was alternatively determined according to Ph. Eur. 2.9.3 Dissolution test for solid dosage forms Apparatus 2 (Paddle apparatus). The dissolution of brexpiprazole was assessed in accordance with the test described in the European Pharmacopoeia, 2.9.3, "Dissolution test for solid dosage forms"—Apparatus 2 (Paddle apparatus)." by using a paddle apparatus with a volume of 1000 ml at a temperature of 37° C., in 0.05M acetate buffer, pH4.5 at 50 rpm, such as a Sotax Smart AT 7.

HPLC

HPLC parameters are as follows:

Column: YMC Pack C18, 3 μm; 150×4.6 mm, 45° C.
Mobile phase: 20 mM Sulfamic Acid pH 1.8/Acetonitrile 70/30
Gradient. Isocratic
Flow: 1.0 ml/min
Injection volume: 10 μl
Detection wavelength: 254 nm Assessing Presence of Primary and/or Secondary Particles Sample is dispersed in water with addition of Tween 80. The dispersion is treated in an ultrasonic bath for 5 min (for control sample no ultrasonification is performed). Particle size measurement is performed by laser light diffraction (wet measurement) (e.g. Malvern Mastersizer 3000). Difference of d(90)/d(10)/d(4,3) with/without ultrasonification is assessed.

Providing Crystalline Brexpiprazole Exhibiting the PSD of the Invention

The crystalline brexpiprazole exhibiting the PSD of the present invention is obtained as follows:

Crude crystalline API is milled either manually (mortar, pistil) or by use of a mill. Preferably a ball mill (e.g. Retsch mill) is used.

A. Comparative Examples

1. Comparative Example A-1

1.1 Preparation of Anhydrate of Compound I:

The anhydrate of Compound I was prepared as follows:

API was prepared by using a Retsch ball mill. Experimental settings were as follows: 35 ml, 100 balls 5 mm, 5×10 min, 25 Hz, addition of water (wet milling).

The particle size distribution (PSD) was measured with a Malvern Mastersizer as disclosed elsewhere herein. The PSD of Compound I is as follows:

d(90) 10.8 μm, d(50) 3 μm, d(10) 0.8 μm 1.2 Preparation of Injectable Preparation Comprising the Anhydrate of Compound I as Prepared in 1.1

Comparative Example A-1 corresponds to "Example A" of CA02871398 and was prepared as disclosed in CA02871398 (pages 54/55, "Test Example 3", "Example A"), with the following components:

| Components | Amount (mg) |
|---|---|
| Anhydrate of Compound 1 | 100.0 |
| Sorbitol | 50.0 |
| Sodium Carboxymethylcellulose | 10 |
| Sodium dihydrogenphosphate dihydrate × 2 $H_2O$ | 0.78 |
| Benzyl benzoate | 1.0 |
| Polysorbate 80 | 1 |
| Sodium hydroxide | q.s. (adjusted to pH 7) |
| Water for injection | q.s. |
| Total | 1 ml |

The injectable preparation was prepared as follows:

Sodium carboxymethylcellulose was dissolved in water (paddle stirrer, 50° C.). Sorbitol, Sodium dihydrogenphosphate dihydrate, Benzyl benzoate und Polysorbate 80 were added and dissolved during continuous stirring.

Approximately 7 ml of the solution were transferred to a mortar. Brexpiprazole Anhydrate was added and suspended by aid of a pistil. pH was adjusted to 7 with NaOH 5N. The volume of the suspension was determined with a measuring glass and concentration of the suspension was adjusted to 100 mg/ml by addition of water.

The composition comprises secondary particles. Accordingly, in FIG. 1 the dissolution profile of this composition is referred to as "Secondary particles".

2 Comparative Example A-2

2.1 Preparation of Anhydrate of Compound I

The anhydrate of Compound I was prepared as follows:
API was prepared by using a Retsch ball mill. Experimental settings were as follows: 35 ml, 100 balls 5 mm, 5×10 min, 25 Hz, addition of water (wet milling).

The particle size distribution (PSD) was measured with a Malvern Mastersizer as disclosed elsewhere herein. The PSD of Compound I is as follows:

d(90) 10.8 µm, d(50) 3 µm, d(10) 0.8 µm

2.2 Preparation of Injectable Preparation Comprising the Anhydrate of Compound I as Prepared in 2.1

Comparative Example A-2 corresponds to "Comparative Example A" of CA02871398 and was prepared as described below, with the following components:

| Components | Amount (mg) |
|---|---|
| Anhydrate of Compound 1 | 100.0 |
| Mannitol | 41.6 |
| Sodium carboxymethylcellulose | 8.32 |
| Sodium dihydrogenphosphate dihydrate × 2 $H_2O$ | 0.78 |
| Sodium hydroxide | q.s. (adjusted to pH 7) |
| Water for injection | q.s. |
| Total | 1 ml |

Sodium carboxymethylcellulose was dissolved in water (paddle stirrer, 50° C.). Mannitol, and Sodium dihydrogenphosphate dihydrate were added and dissolved during continuous stirring.

Approximately 7 ml of the solution were transferred to a mortar. Brexpiprazole Anhydrate was added and suspended by aid of a pistil. pH was adjusted to 7 with NaOH 5N. The volume of the suspension was determined with a measuring glass and concentration of the suspension was adjusted to 100 mg/ml by addition of water.

The composition does not comprise secondary particles, but only primary particles. Accordingly, in FIG. 1 the dissolution profile of this composition is referred to as "Primary particles".

B. Example

1. Preparation of Anhydrate of Compound I

The anhydrate of Compound I was prepared as follows:
API with d(90) 42 µm was prepared by using a mortar and pistil. Crude API was manually milled. After milling the material was sieved through a 50 µm sieve.

API with d(90) 79 µm was prepared by using a Retsch ball mill. Experimental settings were as follows: 35 ml, 1 ball, 15 min, 25 Hz. After milling material was sieved through a 100 µm sieve.

The particle size distribution (PSD) was measured with a Malvern Mastersizer as disclosed elsewhere herein.

The obtained particles respectively exhibited the following PSD:

| (i) | (ii) |
|---|---|
| D(90): 42 µm | D(90); 79 µm |
| D(10): 1.5 µm | D(10): 1.3 µm |
| D(4.3): 19 µm | D(4.3): 30 µm |

2. Preparation of Injectable Preparations Comprising the Anhydrate of Compound I as Prepared in 1

Injectable preparations (aqueous suspensions) comprising brexpiprazole (respectively (i) and (ii)) were prepared with the following components:

| Components | Amount (mg) |
|---|---|
| Anhydrate of Compound I | 100.0 |
| Sodium Carboxymethylcellulose | 10.0 |
| Sodium dihydrogenphosphate dihydrate × 2 $H_2O$ | 0.78 |
| Water for injection | q.s. |
| Total | 1 ml |

Sodium carboxymethylcellulose was dissolved in water (paddle stirrer, 50° C.). Sodium dihydrogenphosphate dihydrate was added and dissolved during continuous stirring.

The solution was transferred to a mortar. Brexpiprazole Anhydrate was added and suspended by aid of a pistil.

The aqueous suspensions (comprising particles (i) and (ii), respectively) did not contain secondary particles of brexpiprazole. In FIG. 1, the dissolution profiles of these compositions are referred to as "42 µm" and "79 µm".

3. Preparation of Injectable Preparations—an Oily Suspension Comprising the Anhydrate of Compound I as Prepared in 1

Injectable preparations (oily suspensions) comprising brexpiprazole (respectively (i)) were prepared with the following components:

| Components | Amount (mg) |
|---|---|
| Anhydrate of Compound I | 100.0 |
| Oil carrier | add to 1 ml |
| Total | 1 ml |

The injectable preparations were stirred gently and shortly until a homogeneous suspension was obtained. Castor oil was used for the experiment shown in example 3, but similar results were obtained with sesame oil and peanut oil.

The oily suspensions (comprising particles of brexpiprazole anhydrate having the particle size distribution (i)) did not contain secondary particles of brexpiprazole.

C. Result

The present inventors have discovered that the burst effect described in WO 2013/161830 A1 can be reproduced in in-vitro dissolution assays. FIG. 1 depicts the dissolution profile of Comparative Example A-1 ("Secondary particles"), Comparative Example A-2 ("Primary Particles"), and the examples according to the present invention (referred to in FIG. 1 as "42 µm" and "79 µm").

The dissolution profile of the aqueous suspension "Primary particles" (1) shows a pronounced burst release, as evidenced by the very quick onset of dissolution. Already after 10 minutes 85% of the brexpiprazole was dissolved (see table below).

In contrast, the dissolution profile of the aqueous suspension "Secondary particles" (2) does not show a burst release and only about 50% of the brexpiprazole were dissolved after 10 minutes.

Surprisingly, the suppression of a burst effect was not dependent on the presence of secondary particles. The dissolution profile of the aqueous suspensions according to the present invention ("42 µm" and "79 µm") did also not show any burst effect and after 10 minutes only 39% and 34%, respectively, of the brexpiprazole were dissolved (see table below).

Dissolution
Paddle, pH 4.5, 100 rpm, 1000 ml

|  |  | Time [min] | | | | | | | | |
|---|---|---|---|---|---|---|---|---|---|---|
|  |  | 5 | 10 | 20 | 30 | 45 | 60 | 90 | 120 | 360 |
| Type of formulation | Primary particles | 79 | 85 | 87 | 88 | 87 | 87 | 87 | 85 | 86 |
|  | Secondary particles | 26 | 49 | 64 | 69 | 74 | 77 | 82 | 84 | 96 |
|  | 42 µm | 24 | 39 | 48 | 54 | 59 | 63 | 67 | 71 | 81 |
|  | 79 µm | 28 | 34 | 40 | 43 | 46 | 48 | 51 | 53 | 62 |

Also dissolution testing in a flow through cell could be used to observe a burst effect in-vitro. While the "Primary particles" (1) showed a pronounced burst release, with 20% of the brexpiprazole dissolved after 180 minutes (see table below), the dissolution profile of the aqueous suspension "Secondary particles" (2) was much slower with only about 4% of the brexpiprazole dissolved after 180 minutes.

Again, and surprisingly, the suppression of a burst effect was not dependent on the presence of secondary particles. The dissolution profile of the aqueous suspension according to the present invention "79 µm" also showed much slower dissolution than the "primary particles" and after 180 minutes only 9% of the brexpiprazole was dissolved.

Flow Through Cell
2 ml/min, 37° C., 0.05M Acetate buffer pH 4.5

|  |  | Time [min] | | | | | |
|---|---|---|---|---|---|---|---|
|  |  | 30 | 60 | 90 | 120 | 180 | 240 |
| Type of formulation | Primary particles | 5 | 11 | 14 | 16 | 20 | 22 |
|  | Secondary particles | 1 | 2 | 3 | 3 | 4 | 5 |
|  | 79 µm | 3 | 5 | 6 | 7 | 9 | 10 |

As demonstrated, an aqueous suspension comprising the crystalline brexpiprazole particles having a PSD as defined in the present invention, exhibits no burst effect and additionally exhibits a delayed release (sustained release) profile. A further advantage is that these improved properties can be beneficially attained without the need to prepare secondary particles suggested in prior art for burst control.

When the oily suspension of example 3 was tested by dissolution testing in a flow through cell and compared with the "Primary particles", which showed a pronounced burst release, and the "Secondary particles", which dissolved much slower, the oily suspension of example 3 behaved very much like the "Secondary particles" and dissolved slowly with only about 3-4% of the brexpiprazole from the oily suspension dissolved after 180 minutes. Castor oil and peanut oily gave very similar results.

Again, and surprisingly, the suppression of a burst effect could also be achieved by an oily suspension of primary particles.

Flow Through Cell
2 ml/min, 37° C., 0.05M Acetate buffer pH 4.5

|  |  | Time [min] | | | | | |
|---|---|---|---|---|---|---|---|
|  |  | 30 | 60 | 90 | 120 | 180 | 240 |
| Type of formulation | Primary particles | 5 | 11 | 14 | 16 | 20 | 22 |
|  | Secondary particles | 1 | 2 | 3 | 3 | 4 | 5 |
|  | Example 3 | 1 | 1 | 2 | 2 | 3 | 4 |

As demonstrated, an oily suspension comprising the crystalline brexpiprazole particles exhibits no burst effect and additionally exhibits a delayed release (sustained release) profile. A further advantage is that these improved properties can be beneficially attained with a simple formulation even in the absence of particle binders and/or further excipients, thereby avoiding the risk of adverse events which could be cause by the particle binders and/or further excipients.

The invention claimed is:

1. Crystalline brexpiprazole, wherein the crystalline brexpiprazole has a particle size distribution (PSD) characterized by a d(90) of 30 µm to 100 µm, by a d(10) of at least 1.0 µm, and by a d(4,3) of at least 15.0 µm, wherein the particle size distribution of said crystalline brexpiprazole is unimodal and, wherein the crystalline brexpiprazole does not comprise any noticeable amounts of secondary particles, wherein noticeable amounts of secondary particles are present in a sample if any of the PSD values d(90), d(10), and d(4,3) assessed after ultrasound treatment of said sample differs by 20% or more from the respective PSD value(s) assessed prior to said ultrasound treatment of said sample.

2. Composition comprising crystalline brexpiprazole according to claim 1, wherein said composition does not comprise any noticeable amounts of secondary particles, wherein noticeable amounts of secondary particles are present in said composition if any of the PSD values d(90), d(10), and d(4,3) assessed after ultrasound treatment of said composition differs by 20% or more from the respective PSD value(s) assessed prior to said ultrasound treatment of said composition.

3. Pharmaceutical composition comprising the crystalline brexpiprazole of claim 1 and one or more pharmaceutically acceptable excipient, wherein said pharmaceutical composition is for reconstitution to form an aqueous suspension for parenteral administration.

4. The pharmaceutical composition according to claim 3, wherein said pharmaceutical composition is a powder.

5. Aqueous suspension obtainable or obtained by combining the crystalline brexpiprazole of claim 1 with an aqueous solution or water, and optionally further pharmaceutically acceptable excipients.

6. The aqueous suspension according to claim 5, wherein the aqueous suspension is in the form of an injectable preparation.

7. The aqueous suspension according to claim 5, which contains crystalline particles of brexpiprazole as the sole solid species.

8. The aqueous suspension according to claim 5, providing a sustained release of brexpiprazole after administration to a patient, wherein the aqueous suspension maintains an effective blood concentration of brexpiprazole for the treatment of schizophrenia, bipolar disorder, or depression, for at least one week.

9. Vial or prefilled syringe comprising the crystalline brexpiprazole of claim 1.

10. Kit including
   (a) a vial or prefilled syringe comprising the crystalline brexpiprazole of claim 1, and
   (b) an aqueous solution or water.

11. Process for the preparation of the aqueous suspension of claim 5 comprising the following steps:
   a) preparing a vehicle, comprising the steps of dissolving one or more of isotonizing agents, stabilizers, viscosity increasing agents, and bulking agents in water, and optionally adjusting the pH by adding buffers or pH adjusters;
   b) optionally, sterilizing the vehicle obtained in step a);
   c) incorporating crystalline brexpiprazole having a particle size distribution as defined in claim 1, thereby obtaining the aqueous suspension;
   d) optionally, carrying out a homogenizing step;
   e) optionally, sterilizing the aqueous suspension.

12. A method for treatment of schizophrenia, bipolar disorder, or depression, comprising administering to a patient a therapeutically effective amount of a pharmaceutical composition comprising the crystalline brexpiprazole of claim 1.

* * * * *